Figure 1:
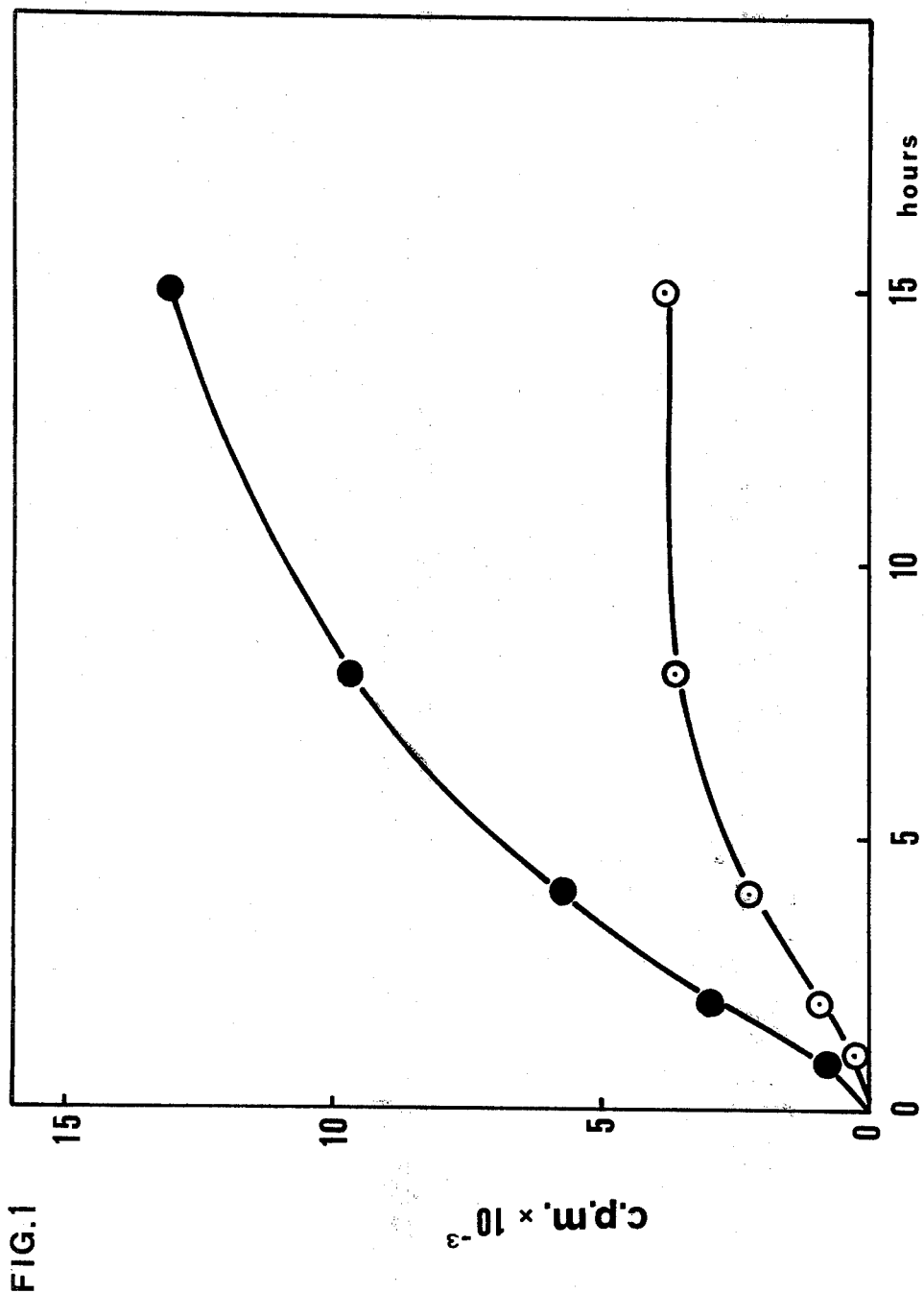

United States Patent [19]

Borgo

[11] 4,386,077
[45] May 31, 1983

[54] PHARMACEUTICAL COMPOSITION FOR ORAL ADMINISTRATION CONTAINING CYTIDINE DIPHOSPHOCHOLINE

[75] Inventor: Eraldo Borgo, Ficarazzi di Catania, Italy

[73] Assignee: Made Italiana s.r.l, Rome, Italy

[21] Appl. No.: 257,538

[22] Filed: Apr. 27, 1981

[51] Int. Cl.$^3$ ............................................. A61K 31/70
[52] U.S. Cl. .................................................... 424/180
[58] Field of Search ......................................... 424/180

[56] References Cited

U.S. PATENT DOCUMENTS 3,666,748  5/1972  Honjo et al. .......................... 424/180
3,872,083  3/1975  Okutsu et al. ......................... 424/180

OTHER PUBLICATIONS

Chem. Abstracts, 86:3549x.
Chem. Abstracts, 94:7656t.
Chem. Abstracts, 91:2794q.

Primary Examiner—Ethel G. Love
Attorney, Agent, or Firm—Bucknam and Archer

[57] ABSTRACT

A pharmaceutical composition suitable for oral administration containing cytidine diphosphocholine (CDP-choline) or a salt thereof in association with substances of the phospholipids group.

3 Claims, 5 Drawing Figures

PHARMACEUTICAL COMPOSITION FOR ORAL ADMINISTRATION CONTAINING CYTIDINE DIPHOSPHOCHOLINE

DESCRIPTION OF THE INVENTION

The present invention refers to a pharmaceutical composition suitable for oral administration containing cytidine diphosphocholine (CDP-choline). More particularly, the present invention refers to a pharmaceutical composition suitable for oral administration containing CDP-choline in association with substances of the phospholipids group.

It is known that cytidine diphosphocholine is employed in the treatment of some pathologic diseases in humans. In particular, the therapeutical indications of CDP-choline are essentially represented by consciousness impairments due to cranial traumas or endogenous affections such as, for instance, hemorrages, cerebral thrombosis, cerebropathies ascribable to atherosclerosis. CDP-choline proved to be useful also in the treatment of the Parkinson-disease and in the Parkinson-like syndromes.

In explaining the therapeutical action of CDP-choline, it must be taken into consideration that this substance is a precursor in the biosynthesis of phospholipids. With this respect, the biochemical meaning of CDP-choline is well acknowledged. In humans, CDP-choline is administered at daily dosage of 100–1000 mg. The usual administration form is generally the parenteral one as an aqueous solution containing from 5 to 25% (weight/volume) of the active ingredient.

The pharmaceutical compositions containing CDP-choline actually employed are, in any case, not suitable for the oral administration. This is a consequence of the poor absorbability of the compound as such and the ease it can be degraded in the gastro-intestinal tract by the enzimes existing therein.

It goes without saying that the lack of an oral formulation containing CDP-choline is a strong limitation to the therapeutical employment of the compound itself. Accordingly, the purpose of the present invention is to provide a pharmaceutical composition containing CDP-choline or a salt thereof as the active ingredient, said composition being able to remove these drawbacks.

This purpose is achieved in the present invention by providing a pharmaceutical composition containing CDP-choline or a salt thereof in chemico-physical association or molecular combination with a substance of the phospholipids group such as, for instance, the lecithins.

The association is preferably prepared by mixing a solution containing CDP-choline or a salt thereof with phospholipids in the solid state or as emulsions or solutions. In order to improve the stability of the preparation, proteinaceous materials and cross-linking agents may also be advantageously added. With respect to the ratio CDP-choline/phospholipids it preferably varies between 1/20 and 1/0.5 (w/w=weight/weight).

As it can be shown from the examples hereinbelow reported (these examples must be considered illustrative, but not limitative of the scope of the invention), the new pharmaceutical compositions possess remarkable advantages over the usual aqueous solutions of CDP-choline which have currently been used in therapy till now. In fact, a noteworthy potentiation of the therapeutical actions of CDP-choline is observed, apart from the possibility of administering this substance by oral route. This is evident from the following examples, wherein the pharmaceutical compositions containing $^{14}$C-labelled CDP-choline are investigated.

EXAMPLE 1

Preparation of CDP-choline in Association with Phospholipids

The association of CDP-choline with phospholipids is obtained according to methods which allow to obtain a composition which is homogeneous from a chemico-physical standpoint and suitable for the pharmaceutical oral administration. The method of preparation can be illustrated as follows: 100 Grams of CDP-choline sodium salt are dissolved in 100 ml of water. Separately, in a container equipped with a stirring system, 400 g of vegetal phospholipids in granules are prepared. The phospholipids granules are uniformly stirred and, while stirring, the aqueous solution of CDP-choline sodium salt is sprayed over these granules, which are subsequently dried in an oven at a 70°–80° C. either in vacuo or not. The so obtained preparation shows, after extraction, an uniform content of CDP-choline in its different parts.

Following substantially the same procedure as above, the ratios CDP-choline/phospholipids has been varied in several experiments, thus obtaining preparations containing the two compounds in weight proportions comprised between 1/20 and 1/0.5.

As stated above, the chemico-physical stability of the pharmaceutical preparations can be improved by adding proteinaceous materials and cross-linking agents.

As a further representative example, the following preparation is reported.

EXAMPLE 2

As described in Example 1, a solution of 100 grams of CDP-choline in 100 ml of water containing 5 grams of serumalbumin (or egg-albumin, or another edible protein) is sprayed on 400 g of phospholipid granules. The so coated granules are then sprayed, again under stirring, with 100 ml of water containing 5% of formaldehyde as cross-linking agent. The obtained material is finally dried as above illustrated.

Oral absorption and distribution of $^{14}$C-labelled CDP-choline associated with phospholipids Analogous formulations as those illustrated in Example 1 have been prepared, but $^{14}$C-CDP-choline is added to the initial solution. The labelled carbon atom is that of the methyl group of the choline moiety. Generally, the radioactivity was 50 μcurie/gram of total CDP-choline.

(a) Aqueous solutions of $^{14}$C-CDP-choline or suspensions of formulations $^{14}$C-CDP-choline/phospholipids obtained as in Example 1 are administered by gastric gavage to rats of average weight of 200 g. The administered amounts correspond to 50 mg of CDP-choline.

At different time intervals a certain amount of blood is collected and, after 24 hours from the beginning of the experiment, the animals are sacrificed. The amount of radioactivity is measured in predetermined serum volumes or weight of the various organs or tissues. The results reported in the following table 1 and the attached drawing indicate that the radioactivity recorded in the serum and the tissues after administration of the pharmaceutical composition containing $^{14}$C-labelled CDP-choline and phospholipids is much higher than that recorded after administration of $^{14}$C-labelled CDP-choline in water.

The data reported in this example clearly show how pharmaceutical compositions containing CDP-choline prepared as described in Example 1 are particularly suitable for the oral administration. Thus, the therapeutical advantages are self-evident: not only a more comfortable administration way is provided for, but also a long-lasting effect after a single administration is achieved, as it can be inferred from the maintenance of high radioactivity levels in the serum.

The diagram in the attached drawing refers to the radioactivity (ordinate), expressed in millicurie per minute (c.p.m.x $10^{-3}$), per time unit (abscissa), wherein the symbol (●) is related to an aqueous solution of $^{14}$C-labelled CDP-choline and the symbol (○) is related to the pharmaceutical composition of the present invention containing $^{14}$C-labelled CDP-choline.

TABLE 1

Radioactivity values in different organs and tissues after 24 hours from the oral administration of an aqueous solution of $^{14}$C-labelled CDP-choline and CDP-choline in association with phospholipids. The values are expressed as c.p.m.x $10^{-3}$/gram of organ or tissue.

| Tissue | $^{14}$C—CDP—choline in H$_2$O | $^{14}$C—CDP—choline plus phospholipids |
|---|---|---|
| Brain | 1.55 | 6.53 |
| Liver | 65.4 | 164.7 |
| Kidney | 46.3 | 52.2 |
| Muscle | 3.1 | 6.1 |

(b) In a further experiment, female Cynomolgus monkeys weighing about 2 kg were intravenously administered with a single dosage of 25 mg/kg of $^{14}$C-labelled CDP-choline with specific activity of 0.1 μCi/mg. Blood was collected at the following time: 0 (basal values) and 5, 10, 15, 30, 60 minutes, 2, 4, 7, 24 and 30 hours after the administration. From the end of the curves serum concentration/time, it was possible to calculate the constant of the apparent elimination speed from the organism as well as the relative half-life. These values were utilized in calculating the AUC $T_{30\ hours} \rightarrow T_\infty$ for the total of the curves concentration/time in the same animal. The AUC $T_o \rightarrow T_{30\ hrs}$ was calculated by means of the trapezium methods. Subsequently, after at least 10-15 days of interval, the same animals were administered with two different dosages of the preparation according to the present invention and two corresponding dosages of CDP-choline as the control (control dosages). The dosages, expressed as CDP-choline, were 200 mg/kg and 400 mg/kg, corresponding to 2 μCi/kg and 4 μCi/kg respectively. For each dosage, a randomized cross-over procedure was used. Seriated blood samples were collected until 30 hours after each administration. From the single curves concentration/time it was possible to calculate the AUC $T_o \rightarrow T_{30\ hrs}$. After each administration, including the intravenous one, urine was collected at the following time intervals: 0-24 hours, 24-48 hours and 48-72 hours.

Figure 2:
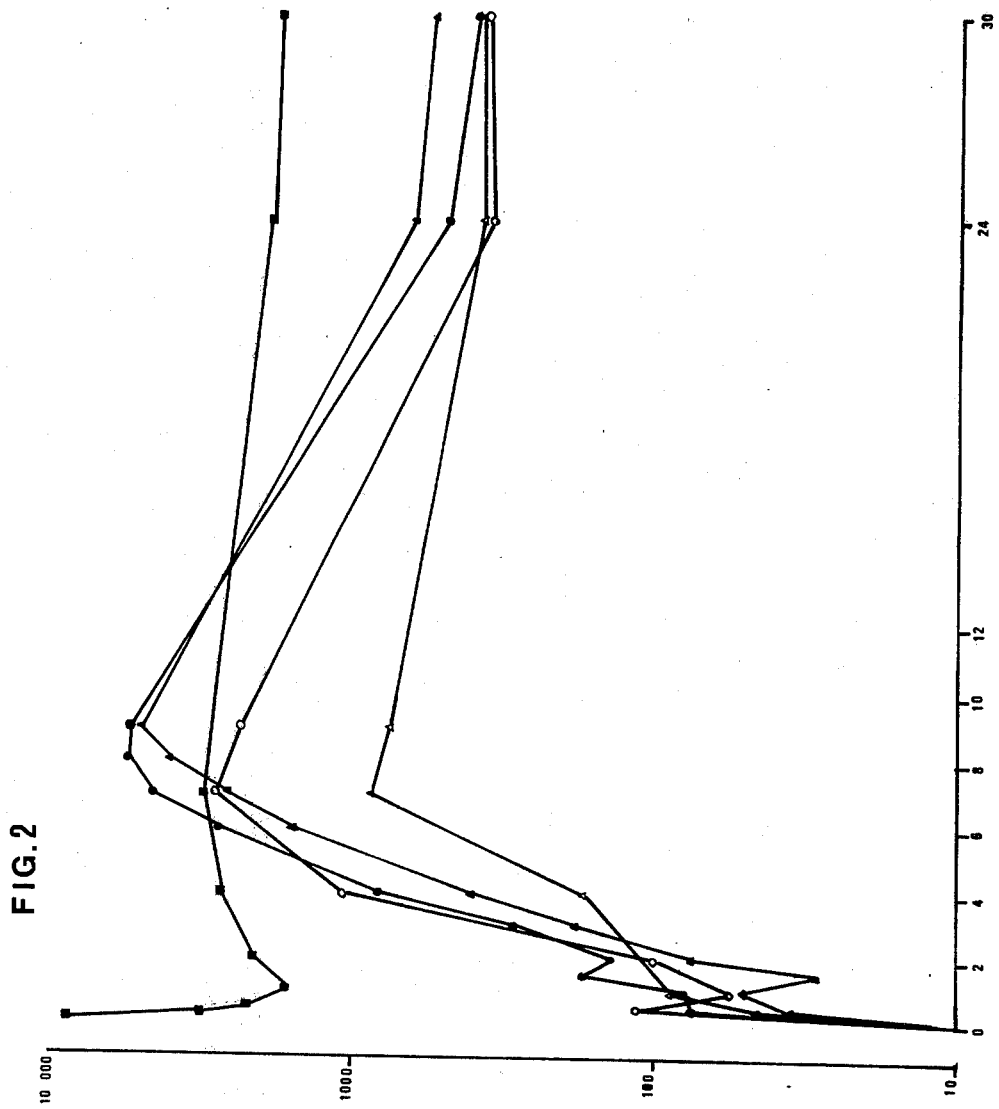
Figure 3:
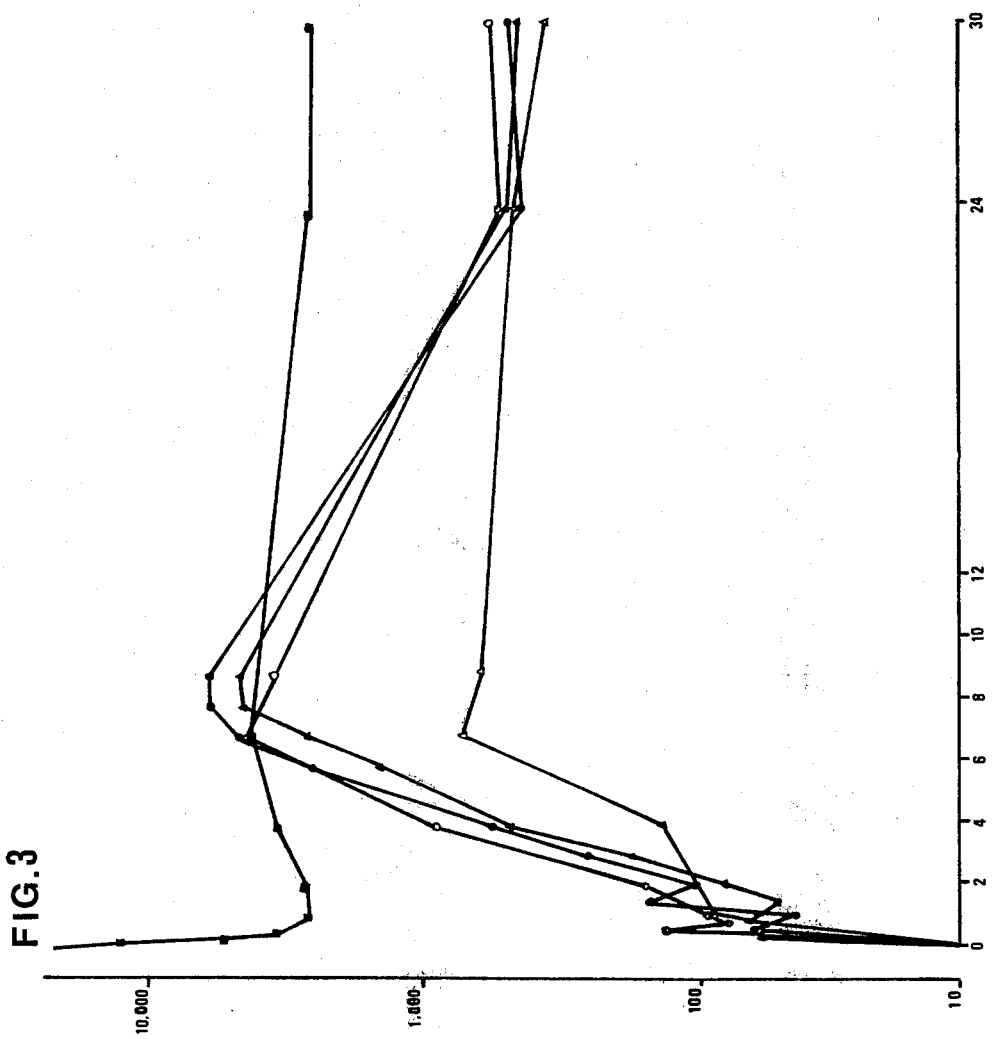

The results obtained with each single animal are reported in Table II and III and FIGS. 2 and 3, whereas Table IV refers to the means and relative standard deviations of the two animals.

Figure 4:
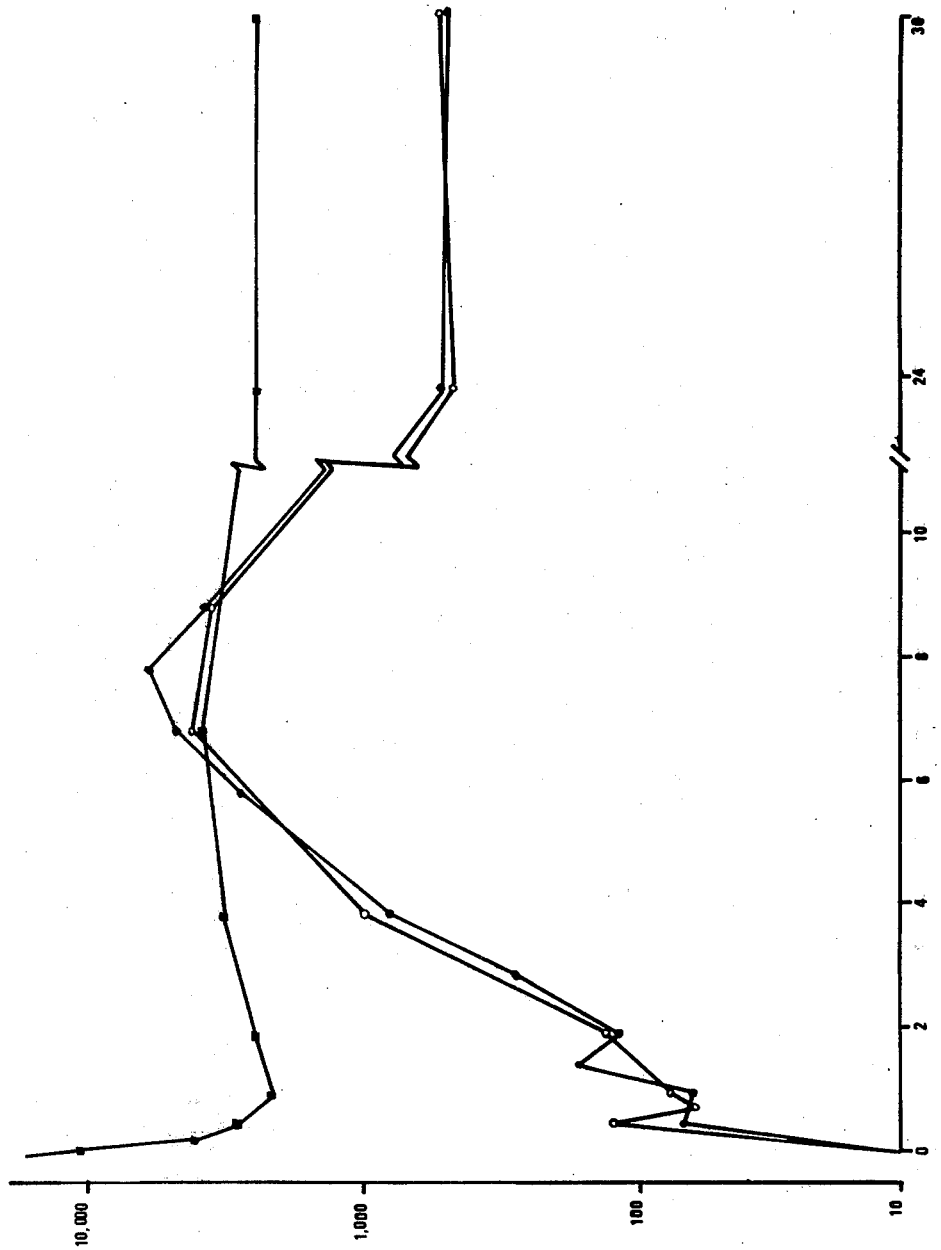
Figure 5:
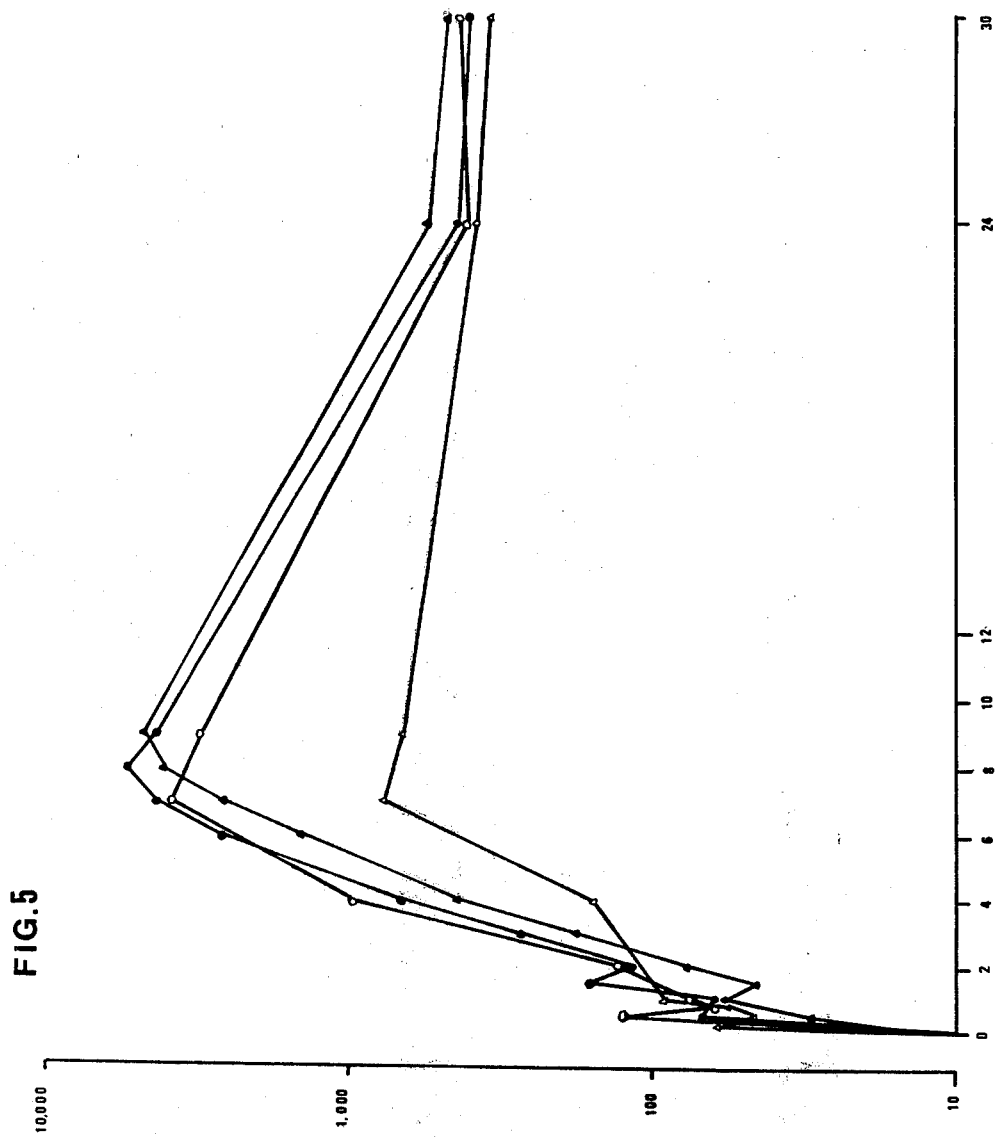

In FIG. 4 a comparison is carried out between the curve mean concentration/time following the intravenous administration of CDP-choline and the curves mean concentration/time following the administration of the two above dosages of the preparation according to the invention ("ASONIC"). Finally, FIG. 5 refers to the comparison between the kynetic of the two oral dosages of the pharmaceutical preparation according to the invention and the two corresponding control dosages of CDP-choline. At the tested dosages, the pharmaceutical composition object of the present invention displays a remarkable oral absorption, as it can be seen from the maximum concentration peak which is reached earlier than with the administration of the control dosages. The maximum reachable concentration with both dosages of the preparation according to the invention is decidedly higher than that reachable with the control dosages of CDP-choline: particularly evident is the difference at the lower dose. The absolute bioavailability of the pharmaceutical composition of the present invention in monkeys proved to be higher than 50%: the following F values at the following CDP-choline dosages were obtained 200 mg/kg → F = 0.5109

400 mg/kg → F = 0.7781 whereas the absolute bioavailability of the corresponding control dosages of CDP-choline proved to be much lower, the following F values being obtained 200 mg/kg → F = 0.2143

400 mg/kg → F = 0.6174

The pharmaceutical composition of the present invention is thus absorbed at a large extent and, apparently, the percent absorption increases with the dosage.

TABLE II

| Cynomolgus monkey no. 1 female sex Weight: kg 2 | | "ASONIC" (CDP—choline + phospholipids) comparison with CDP—choline | | | |
|---|---|---|---|---|---|
| | SERUM CONCENTRATIONS DPM/ml | | | | |
| | CDP—choline | CDP—choline × os | | "ASONIC" per os | |
| Time | 25 mg/kg i.v. = 2.5 μCi/kg | 200 mg/kg 2 μCi/kg | 400 mg/kg 4 μCi/kg | 200 mg/kg 2 μCi/kg | 400 mg/kg 4 μCi/kg |
| 5' | 8708 | — | — | — | — |
| 15' | 3169 | — | — | — | — |
| 30' | 2226 | 45 | 35 | 116 | 75 |
| 45' | — | 53 | — | 46 | — |
| 60' | 1629 | 88 | 52 | 57 | 80 |
| 90' | — | — | 29 | — | 172 |
| 2 hr | 2165 | — | 75 | 102 | 138 |
| 3 hr | — | — | 187 | — | 294 |

TABLE II-continued

| | | | | | |
|---|---|---|---|---|---|
| 4 hr | 2760 | 172 | 401 | 1072 | 815 |
| 6 hr | — | — | 1590 | — | 2753 |
| 7 hr | 3120 | 852 | 2712 | 3784 | 4560 |
| 8 hr | — | — | 4092 | — | 5495 |
| 9 hr | — | 743 | 5175 | 3049 | 5399 |
| 24 hr | 1812 | 339 | 622 | 358 | 481 |
| 30 hr | 1749 | 385 | 540 | 360 | 385 |
| $\beta$ | 0.0315 | — | — | — | — |
| $\frac{1}{2}$ | 22 hr | — | — | — | — |
| $AUC_0^{30\ hr}$ | 72475 | 14053 | 59643 | 42839 | 89465 |
| $AUC_0^{\infty}$ | 127999 | 26275 | 76786 | 54268 | 102087 |
| CUMULATIVE URINARY ELIMINATION, % OF THE ADMINISTERED DOSE | | | | | |
| 0–24 hr | 49 | 38.4 | 24.7 | 44.4 | 35.9 |
| 24–48 hr | 1.8 | 6.2 | 6.0 | 3.9 | 5.4 |
| 48–72 hr | 0.4 | 0.7 | 0.6 | 1.1 | 0.9 |
| 0–72 hr | 51.2 | 45.3 | 31.3 | 49.4 | 42.2 |

TABLE III

| Cynomolgus Monkey no. 2 Female sex Weight: 2 kg | | "ASONIC" (CDP—choline + phospholipids comparison with CDP—choline | | | |
|---|---|---|---|---|---|
| SERUM CONCENTRATIONS DPM/ml | | | | | |
| | CDP—choline | CDP—choline per os | | "ASONIC" per os | |
| Times | 25 mg/kg i.v. = 2.5 µCi/kg | 200 mg/kg = 2 µCi/kg | 400 mg/kg = 4 µCi/kg | 200 mg/kg = 2 µCi/kg | 400 mg/kg = 4 µCi/kg |
| 5' | 12414 | — | — | — | — |
| 15' | 5007 | 61 | — | — | — |
| 30' | 3467 | — | — | 135 | 64 |
| 45' | — | 59 | — | 78 | — |
| 60' | 2625 | 94 | 69 | 93 | 45 |
| 90' | — | — | 52 | — | 152 |
| 2 hr | 2630 | — | 81 | 159 | 100 |
| 3 hr | — | — | 174 | — | 250 |
| 4 hr | 3369 | 135 | 495 | 884 | 545 |
| 6 hr | — | — | 1.401 | — | 2.491 |
| 7 hr | 4013 | 696 | 2.560 | 4.150 | 4.204 |
| 8 hr | — | — | 4.235 | — | 5.345 |
| 9 hr | — | 595 | 4.450 | 3.250 | 5.360 |
| 24 hr | 2258 | 417 | 449 | 452 | 393 |
| 30 hr | 2145 | 303 | 401 | 483 | 415 |
| $\beta$ | 0.02949 | — | — | — | — |
| $\frac{1}{2}$ | 23.5 | — | — | — | — |
| $AUC_0^{30\ hr}$ | 86516 | 12.688 | 51.491 | 46.772 | 62.635 |
| $AUC_0^{\infty}$ | 159254 | 22.963 | 65.089 | 63.151 | 76.708 |
| CUMULATIVE URINARY ELIMINATION, % OF THE ADMINISTERED DOSE | | | | | |
| 0–24 hr | 52.3 | 47.1 | 37.9 | 43.5 | 38.8 |
| 24–48 hr | 3.2 | 2.2 | 5.2 | 7.8 | 9.3 |
| 48–72 hr | 0.3 | 0.4 | 0.9 | 1.2 | 1.6 |
| 0–72 hr | 55.8 | 49.7 | 44.0 | 52.5 | 49.7 |

TABLE IV

| KINETIC OF "ASONIC" IN THE CYNOMOLGUS MONKEYS Comparison with CDP—choline | | | | | |
|---|---|---|---|---|---|
| PLASMATIC CONCENTRATIONS, (AVERAGES AND S.D. OF 2 ANIMALS) DPM/ml serum | | | | | |
| | CDP—choline | CDP—choline × os | | "ASONIC" × os | |
| Times | 25 mg/kg i.v. = 2.5 µCi/kg | 200 mg/kg = 2 µCi/kg | 400 mg/kg = 4 µCi/kg | 200 mg/kg = 2 µCi/kg | 400 mg/kg = 4 µCi/kg |
| 5' | 10561 ± 2620 | — | — | — | — |
| 15' | 4088 ± 1299 | 61 | — | — | — |
| 30' | 2846 ± 877 | 45 | 35 | 125 ± 13.4 | 69.5 ± 7.8 |
| 45' | — | 56 ± 4 | — | 62 ± 23 | — |
| 60' | 2127 ± 704 | 91 ± 4.2 | 61 ± 12 | 75 ± 25 | 62.5 ± 25 |
| 90' | — | — | 40 ± 16 | — | 162 ± 14 |
| 2 hr | 2397 ± 329 | — | 78 ± 4.2 | 131 ± 40.3 | 119 ± 27 |
| 3 hr | — | — | 181 ± 9.2 | — | 272 ± 31 |
| 4 hr | 3064 ± 431 | 154 ± 26 | 448 ± 66 | 978 ± 133 | 272 ± 31 |
| 6 hr | — | — | 1496 ± 134 | — | 680 ± 191 |
| 7 hr | 3566 ± 631 | 774 ± 110 | 2636 ± 107 | 3967 ± 259 | 4382 ± 252 |
| 8 hr | — | — | 4163 ± 101 | — | 5420 ± 106 |
| 9 hr | — | 669 ± 105 | 4813 ± 513 | 3149 ± 142 | 3379 ± 28 |
| 24 hr | 2035 ± 315 | 378 ± 55 | 536 ± 122 | 405 ± 66 | 437 ± 62 |
| 30 hr | 1947 ± 280 | 344 ± 58 | 470 ± 98 | 421 ± 87 | 400 ± 21 |

TABLE IV-continued
KINETIC OF "ASONIC" IN THE CYNOMOLGUS MONKEYS
Comparison with CDP—choline

| | | | | | |
|---|---|---|---|---|---|
| $\beta$ | $0.03049 \pm 0.0014$ | | | | |
| $t$ | $22.75 \pm 1.06$ | | | | |
| $AUC_0^{30hr}$ | $79495 \pm 9924$ | $13370 \pm 965$ | $55567 \pm 5764$ | $44806 \pm 2781$ | $76250 \pm 19254$ |
| $AUC_0^{\infty}$ | $143626 \pm 22100$ | $24619 \pm 2342$ | $70937 \pm 8271$ | $58709 \pm 6281$ | $89397 \pm 17946$ |

CUMULATIVE URINARY ELIMINATION, % OF THE ADMINISTERED DOSE

| | | | | | |
|---|---|---|---|---|---|
| 0–24 hr | $50.65 \pm 2.33$ | $42.75 \pm 6.15$ | $31.3 \pm 9.3$ | $43.95 \pm 0.64$ | $37.35 \pm 2.05$ |
| 24–48 hr | $2.5 \pm 0.99$ | $4.2 \pm 2.83$ | $5.6 \pm 0.56$ | $5.85 \pm 2.76$ | $7.35 \pm 2.76$ |
| 48–72 hr | $0.35 \pm 0.07$ | $0.55 \pm 0.21$ | $0.75 \pm 0.21$ | $1.15 \pm 0.07$ | $1.25 \pm 0.49$ |
| 0–72 hr | $53.5 \pm 3.25$ | $47.5 \pm 3.11$ | $37.65 \pm 8.98$ | $50.95 \pm 2.19$ | $45.95 \pm 5.3$ |

CONCLUSIONS (1) The results obtained with monkeys demonstrate that the pharmaceutical preparation according to the invention possesses a good absolute bioavailability in comparison with intravenous CDP-choline, being higher than 50% at the lower dosage and nearly 80% at the higher dosage. On the other hand, the investigations carried out on rats have pointed out to an almost total absorption of the administered amount.

(2) The kynetic and the oral bioavailability of the pharmaceutical composition object of the present invention are considerably improved, because the absorption occurs more rapidly and is saturated at low doses. Moreover the percent absorption in monkey is higher than that observed with the control dosages of CDP-choline.

The present invention has been illustrated with particular reference to some specific embodiments but this must not be construed as a limitation of the scopes of the invention itself.

I claim:

1. A pharmaceutical composition for the treatment of consciousness impairment in an animal, cerebral thrombosis, cerebropathies ascribable to atherosclerosis, in a form suitable for oral administration, containing CDP-choline or a salt thereof in association with a material containing phospholipids, in the ratio of 1:20–1:0.5% weight by weight, in unit dosage form containing 200 mg up to 400 mg of said CDP-choline or salt thereof per kilogram of body weight of said animal.

2. The method of preparing an association of CDP-choline or a salt thereof with phospholipids which consists of mixing an aqueous solution of CDP-choline or a salt thereof with phospholipids in the solid state or in an emulsion or as a solution in the ratio of 1:20–1:0.5% weight by weight and isolating said association product from the mixture.

3. A pharmaceutical composition according to claim 1, which additionally contains an edible protein in the amount of 5% based on the weight of said CDP-choline or salt thereof and a cross-linking agent in the amount of 5% based on the weight of said CDP-choline or salt thereof.

* * * * *